(12) United States Patent
Koridze

(10) Patent No.: US 6,909,009 B2
(45) Date of Patent: Jun. 21, 2005

(54) ALKANE AND ALKANE GROUP DEHYDROGENATION WITH ORGANOMETALLIC CATALYSTS

(76) Inventor: Avtandil Koridze, Pyliugin Street, 26 Corp. 2, Apartment 511, Moscow (RU), 117393

( * ) Notice: Subject to any disclaimer, the term of this patent is extended or adjusted under 35 U.S.C. 154(b) by 0 days.

(21) Appl. No.: 10/469,960

(22) PCT Filed: Mar. 8, 2002

(86) PCT No.: PCT/IB02/02136
§ 371 (c)(1),
(2), (4) Date: Feb. 3, 2004

(87) PCT Pub. No.: WO02/085920
PCT Pub. Date: Oct. 31, 2002

(65) Prior Publication Data
US 2004/0116727 A1 Jun. 17, 2004

Related U.S. Application Data
(60) Provisional application No. 60/273,772, filed on Mar. 8, 2001.

(51) Int. Cl.$^7$ .......................... C07F 17/02; B01J 31/00; C07C 5/333

(52) U.S. Cl. ............................. 556/22; 556/23; 556/28; 556/30; 585/660; 502/153; 502/154; 502/155; 420/900

(58) Field of Search ............................. 556/22, 23, 28, 556/30; 585/660; 502/153, 154, 155; 420/900

(56) References Cited
U.S. PATENT DOCUMENTS

| | | |
|---|---|---|
| 5,780,701 A | 7/1998 | Kaska et al. |
| 6,072,067 A | 6/2000 | VanBeek et al. |
| 6,074,447 A | 6/2000 | Jensen |
| 6,124,488 A | 9/2000 | Gruter et al. |
| 2001/0039349 A1 | 11/2001 | Hartwig et al |
| 2002/0022733 A1 | 2/2002 | Grubbs et al. |

OTHER PUBLICATIONS

Szymoniak, Jan et al New Heterodifunctional Ligands for Organotransiton —Metal Chemistry: $Ph_2P(CH_2)_nC_5Me_4H$ (n=2), J. Org. Chem. 1990, 55, 1429–1432.
Gusev, Dmitry G. et al "Hydride, Borohydride, and Dinitrogen Pincer Complexes of Ruthenim", Organometallics 2000, 19, 3429–3434.
Jensen, Craig M. "Iridium PCP Pincer Complexes: Highly Active and Robust Catalysts for Novel Homogeneous Aliphatic Dehydrogenations", Chem. Commun., 1999, 2443–2449.
Arndtsen, Bruce A. et all "Selective Intermolecular Carbon—Hydrogen Bond Activation by Synthetic Metal Complexes in Homogeneous Solution", Acc. Chem. Res. 1995, 28, 154–162.

Nemeh et al "Interaction of {2,6—Bis–[(di–tert–butylphosphino)methyl]phenyl}rhodium(I) with Hydrocarbons, X—ray Molecular Structure of {2,6—Bis–[(di–tert–butylphosphino)methyl]phenyl}chlorohydrido–rhodium(III)", Organometallics 1983, 2, 1442–1447.
Moulton, Christopher J. et al "Transition Metal—Carbon Bonds, Part XLII Complexes of Nickel, Palladium, Platinum, Rhodium and Iridium with the Tridentate Ligand 2,6–Bis[(Di–t–butylphosphino)methyl]phenyl", J.C.S. Dalton, 1976, p1020–1024.
Nemeh, Saad et al "Iridium Chemistry of 1,6–Bis((tert–butylphosphino)methyl)–1,3,5–cycloheptatriene", Organometallics 1998, 17, 2003–2008.
Gupta, Mukta et al "Catalytic Dehydrogenation of Cycloalkanes to Arenes by a Dihydrido Iridium P–C–P Pincer complex", J. Am. Soc. Chem. 1997, 119, 840–841.
Gupta, Mukta et al "A highly active alkane dehydrogenation catalyst: stabilization of dihydrido rhodium and iridium complexes by a P–C–P pincer ligand", Chem. Commun., 1996, 2083–2084.
Xu, Wei–wei et al "Thermochemical alkane dehydrogenation catalyzed in solution without the use of a hydrogen acceptor", Chem. Commun., 1997, 2273–2274.
Chemical Abstracts, vol. 132, No. 12, 2000, p. 704, 132:151839a.
Chemical Abstracts, vol. 132, No. 17, 2000, p. 777, 132:222645x.
Chemical Abstracts, vol. 131, No. 5, 1999, p. 674, 131:58960c.
Chemical Abstracts, vol. 131, No. 16, 1999, p. 719, 131:214405h.
Chemical Abstracts, vol. 130, No. 23, 2000, p. 717, 130:311920j.
Chemical Abstracts, vol. 130, No. 26, 2000, p. 642, 130:351943a.
Chemical Abstracts, vol. 133, No. 3, 2000, p. 551, 133:30821a and 133:30822b.
Chemical Abstracts, vol. 132, No. 17, 2000, p. 774, 132:222623p.
Chemical Abstracts, vol. 132, No. 5, 2000, p. 707, 132:50116g.
Chemical Abstracts, vol. 132, No. 1, 2000, p. 419, 132:3436b.

(Continued)

*Primary Examiner*—Porfirio Nazario-Gonzalez

(57) ABSTRACT

Novel polynuclear organometallic complexes useful as catalysts for the reversible deshydrogenation of alkanes and alkane group are disclosed. The novel compounds comprise a first transition, a second transition metal p-bonded to an ?5-aromatic ligand, and a pincer ligand. The pincer ligand comprises a 6p-electron aromatic ring having at least 2 ring atoms in an 1, 3 relationship bonded each to a neutral Lewis base through a bridge, the bridge being a diradical. The pincer ligand binds the first transition metal through each of the Lewis bases and through the ring atom adjacent to both Lewis bases and p-coordinates the second transition metal through all aromatic ring atoms. The first transition metal may also bond to 2 or 4 hydrogen atoms.

22 Claims, No Drawings

OTHER PUBLICATIONS

Chemical Abstracts, vol. 132, No. 8, 2000, p. 723, 132:93448j.
Chemical Abstracts, vol. 130, No. 1, 1999, p. 469, 130:3947c.
Chemical Abstracts, vol. 130, No. 21, 1999, p. 721, 130:282156g.
Chemical Abstracts, vol. 130, No. 17, 1999, p. 718, 130:223481m.
Chemical Abstracts, vol. 132, No. 19, 2000, p. 672, 132:251223p.
Chemical Abstracts, vol. 132, No. 23, 2000, p. 706, 132:308487j.
Chemical Abstracts, vol. 126, No. 12, 1997, p. 601, 126:157608x.
Haenel, Mattias W. et al "Thermally Stable Homogeneous Catalysts for Alkane Dehydrogenation" Angew. Chem. Int. Ed. 2001, 40, No. 19 p 3596–3600.
Nemeh, Saadallah N. "Reactions of Rhodium(I) and Iridium(I) Complexes with Aromatic and Suturated Hydrocarbons", Thesis, University of California, Dec. 1983.
Niu, Shuqiang et al "Theoretical Studies of Inorganic and Organometallic Reaction Mechanisms. 15. Catalystic Alkane Dehydrogenation by Iridium(III) Complexes", J. Am. Chem. Soc. 121(16), 3992–3999, Apr. 7, 1999.
"Reactions of Transition–Metal Complexes", Chemical Reviews, 2000, vol. 100, No. 2, p395–396.
Farrington, Edward J. et al, "Synthesis and reactivity of a ferrocene–derived PCP–pincer ligand", Chemial Communications, 2002, (4), pp 308–309.

ALKANE AND ALKANE GROUP DEHYDROGENATION WITH ORGANOMETALLIC CATALYSTS

CROSS REFERENCE TO RELATED APPLICATIONS

This application claims priority from PCT/IB02/02136 filed on Mar. 8, 2002 which claims priority of U.S. Provisional Application, Ser. No. 60/273,772 filed on Mar. 8, 2001.

FIELD OF INVENTION

The present relates to a class of organometallic complexes that are useful as catalysts for the reversible dehydrogenation of alkanes and alkane groups and, to intermediates for the preparation thereof.

BACKGROUND OF THE INVENTION

The catalytic dehydrogenation of aliphatic C—H bonds is of major industrial importance. During the past decade there has been a steady progress in the development of soluble transition metal complexes as catalysts for the dehydrogenation of alkanes at moderate conditions. U.S. Pat. No. 5,780,701 discloses an iridium (III) catalytic system (PCP) $IrH_2$ [PCP=$\eta^3$—$C_6H_3(CH_2P(Bu^t)_2)_2$)—1,3], a highly active, homogeneous catalyst for the dehydrogenation of cylcoalkanes at about 200° C. Iridium and rhodium complexes PCP pincer ligands have unusually high thermal stabilities. The key to their effectiveness appears to be their long-term stability even at 200° C. However the production of terminal olefins via the pincer catalyst is limited by the required consumption of a stochiometric amount of a sacrificial hydrogen acceptor and also by the secondary catalytic isomerisation of the terminal olefin to internal isomers.

SUMMARY OF THE INVENTION

In one aspect, the invention provides compounds in which the arene ring in a monoanionic aryl PCP pincer ligand is coordinated to a second transition metal in an $\eta^6$-bonding mode, which may by example provide a means of varying the electron density at the catalytic site by varying the nature of the π-bound metal.

In some embodiments, the present invention provides a polynuclear organometallic compound comprising a tripodal pincer ligand having at least one aromatic ring and two neutral Lewis bases each of which being indirectly linked to the aromatic ring through a bridge. The pincer ligand coordinates to a first transition metal through each of the Lewis bases and through another atom via a σ bond. The aromatic ring of the pincer ligand is π-bonded to a second transition metal with all aromatic ring atoms being involved in the bonding.

In some embodiments, compounds of this invention may comprise a first transition metal selected from the group consisting of Rh and Ir, a second transition metal selected from the group consisting of Fe, Ru, Os, Rh and Ir and being π-bonded to an $\eta^5$-aromatic ligand, and a pincer ligand comprising a 6π-electron aromatic ring having at least 2 ring atoms in an 1, 3 relationship bonded each to a neutral Lewis base through a bridge, the bridge being a diradical and wherein the pincer ligand binds the first transition metal through each of the Lewis bases and through the ring atom adjacent to both Lewis bases and π-coordinates the second transition metal through all aromatic ring atoms. The first transition metal may also bond to 2 or 4 hydrogen atoms, preferably to 2 hydrogen atoms when the first transition metal is Rh.

In some embodiments, the compounds of this invention may be positively charged depending on the number of valence electrons of each transition metal and redox state of the compounds. The counter anion(s) provided to balance the positive charge(s) may be for example $PF6^-$ or $BF4^-$.

In some embodiments, the $\eta^5$-aromatic ligand bonded to the second transition metal may be selected from the group consisting of cyclopentadienyl and substituted cyclopentadienyl, wherein the substituents are selected from the group consisting of optionally substituted $C_1$–$C_4$ alkyl, optionally substituted arylalkyl or heteroarylalkyl in which the alkyl chain contains 1 to 4 carbons, optionally substituted aryl or heteroaryl or when two substitutents are ortho to each other they can together form a saturated, unsaturated or aromatic cyclic structure which can be substituted and contain heteroatoms. Preferably the $\eta^5$-aromatic ligand is cyclopentadienyl, cyclopentadienyl substituted with 1 to 5 substituted alkyls, optionally substituted indenyl and optionally substituted fluorenyl.

In some embodiments, the 6π-aromatic ring of the pincer ligand may be selected from the group consisting of phenyl, substituted phenyl, pyridine, substituted pyridine, cyclopentadienyl and substituted cyclopentadienyl, wherein the substituents are selected from the group consisting of optionally substituted $C_1$–$C_4$ alkyl, alkylsilyl in which the alkyl chains contain 1 or 2 carbons; optionally substituted arylalkyl or heteroarylalkyl in which the alkyl chain contains 1 to 4 carbons, optionally substituted aryl or heteroaryl and where the substitutents may be the same or different and when two substitutents are ortho to each other they can together form a saturated, unsaturated or aromatic cyclic structure which can be substituted and contain heteroatoms.

In some embodiments, compounds of this invention may comprise a second pincer ligand coordinated to a third transition metal as previously described and whose 6π-aromatic ring is also the $\eta^5$-aromatic ligand bonded to the second transition metal.

In some embodiments, the Lewis bases of the pincer ligand may be selected from the group consisting of of —PR'R", —AsR'R" and —SbR'R" wherein R' and R" independently of one another are an optionally substituted alkyl, an optionally substituted cycloalkyl, optionally substituted aryl or heteroaryl.

In some embodiments, the bridges that linked the Lewis bases to the pincer ligand may be diradicals that may be the same or different and may be selected from the group consisting of —$CH_2$—, —$CH_2$—$CH_2$, —CH=CH— and —O—. Preferably the bridges are both —$CH_2$—, or —$CH_2$— and —$CH_2$—$CH_2$, or —$CH_2$— and —CH=CH—.

This invention also provides methods of making compounds of the invention wherein the 6π-aromatic ring of the pincer ligand is π-bonded to an optionally substituted cyclopentadienyl transition metal complexe. Polynuclear organometallic compounds wherein the 6π-aromatic ring of the pincer ligand is phenyl or substituted phenyl, may be prepared by reacting known organometallic compounds having a transition metal coordinated to a monoanionic aryl tridendate pincer ligand with another transition metal π-bonded to an optionally substituted cyclopentadienyl ligand. Polynuclear organometallic compounds wherein the 6π-aromatic ring of the pincer ligand is cyclopentadienyl or substituted cyclopentadienyl, may be prepared by reacting novel intermediates consisting of a transition metal sandwiched between two cyclopentadienyl rings, one of which at least having at least two ring atoms in an 1,3 relationship each indirectly linked to neutral Lewis base, with a suitable source of another transition metal.

In another aspect, this invention may also provide a process of converting an alkane or an alkyl-containing compound into a corresponding olefinic compound comprising contacting the alkane or alkyl-containing compounds under conditions conductive to dehydrogenation with a composition comprising a compound of the invention.

In another aspect, this invention may also provide the use of a compound of the invention to cyclically stored and released hydrogen. In some embodiments, the compounds of the invention catalytically dehydrogenate alkanes and alkane groups, at temperatures between about 60° C. and about 250° C. In some embodiments, the oxidation state at the π-coordinated metal center may be modified to catalyse the reverse reaction, i.e. hydrogenation of unsaturated substrates. By combination of the two reactions, dehydrogenation of alkanes and alkane groups, and hydrogenation of alkenes and other unsaturated hydrocarbons, hydrogen can be cyclically stored and released for applications.

DETAILED DESCRIPTION OF THE INVENTION

Definitions

A "tripodal pincer ligand" or "pincer ligand" as used herein denotes a ligand capable of bonding to a transition metal through three atoms, two of which act as two-electron donors and the third of which acts as a one-electron donor.

A "Lewis base" as defined herein refers to a two-electron donor atom.

The term "diradical" as used herein denotes a chemical entity that has two free valencies. A diradical may be an atom or group of atoms, and may include for example —CH$_2$—, —CH$_2$—CH$_2$, —CH=CH— and —O—.

A "6π-aromatic ring" as used herein refers to a phenyl, a substituted phenyl, a cyclopentadienyl anionic or substituted cyclopentadienyl anionic ring.

Description

In some embodiments, this invention utilizes the π-bonding capability of an arene ring present in a tripodal pincer ligand to coordinate to transition metals in an η$^6$-bonding fashion to provide novels polynuclear organometallic compounds wherein the pincer ligand is η$^3$-coordinated to one transition metal and is η$^6$-bonded to a different transition metal through the arene ring of the pincer ligand.

The present invention may provide a polynuclear organometallic compound comprising a tripodal pincer ligand having at least one 6π-aromatic ring and two neutral Lewis bases which are individually linked to the aromatic ring through a bridge. The pincer ligand coordinates to a first transition metal through each of the Lewis bases and through another atom via a σ bond. The length of the bridge is selected such as to permit η$^3$-coordination of the pincer ligand to the first transition metal. The aromatic ring of the pincer ligand is π-bonded to a second transition metal with all aromatic ring atoms being involved in the bonding. Preferably compounds of the invention have a cyclopentadienyl ligand η$^5$-bonded to the second transition metal. Skeletal frameworks for the compounds of the invention may include for example the following structures:

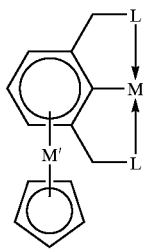
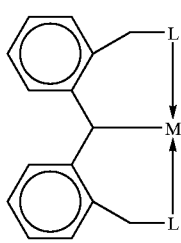
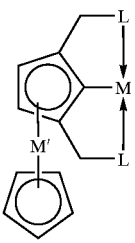
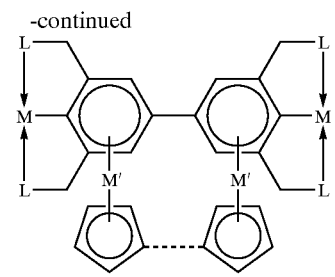
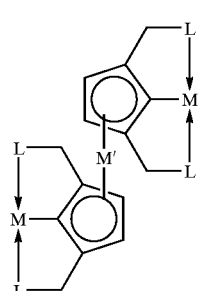
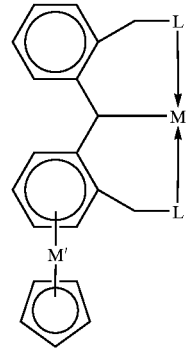
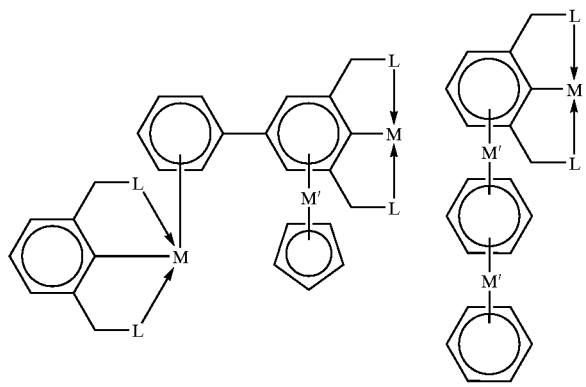
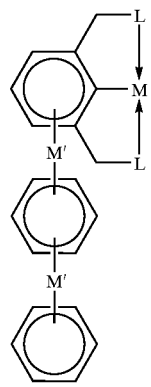

Wherein M and M' are transition metals and L is a Lewis base ligand.

For dehydrogenation catalysis purposes compounds of the invention may preferably have the first transition metal selected from the group of Rh, and Ir.

In one embodiment of the invention, the compound of the invention is a binuclear organometallic compound of formula (I):

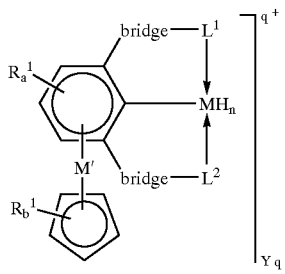

wherein:
M is Rh, Ir;
M' is Fe, Ru, Rh, Os, or Ir;
L$^1$ and L$^2$ independently of one another are —PR'R", —AsR'R" or —Sb R'R"; wherein R' and R" independently of one another are wherein R' and R" independently of one another are an optionally substituted alkyl, an optionally substituted cycloalkyl, and an optionally substituted aryl, or heteroaryl.

each bridge is the same or different and is a diradical;

$R^1$ and $R^2$ independently of one another are hydrogen, optionally substituted $C_1$–$C_4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where $R^1$s and $R^2$s may be the same or different and when ortho to each other can together form a saturated, unsaturated or aromatic cyclic structure which can be substituted and contain heteroatoms.

a is the number of substituents $R^1$ and is ranging from 0 to 3 inclusive;

b is the number of substituents $R^2$ and is ranging from 0 to 5 inclusive;

n is an integer equal to 2 when M is Rh and equal to 2 or 4 when M is Ir;

q is an integer equal to 1 when M is Fe, Ru or Os and equal to 2 when M' is Rh or Ir; and Y is a counter anion that provides the required charge balance.

The Lewis bases L1 and L2 may be the same or different and are preferably selected from group 15 of the Periodic Table. Lewis bases are preferably phosphino groups having bulky substitutents such as tert-Butyl, cyclohexyl and isopropyl.

Compounds of formula (I) are prepared from mononuclear pincer complex precursors by reaction with cyclopentadienyl transition metal complexes in a solvent such as acetone, methylene chloride, tetrahydrofuran. The mononuclear pincer complexes may be made according to literature procedures (see for example U.S. Pat. No. 5,780,701 and references therein). Sources of cyclopentadienyl complexes may include for example $[C_5(CH_3)_5M'(CH_3CN)_3]^+$, $[C_5H_5M'(CH_3CN)_3]^+$, $[C_5H_5M'(CH_3COCH_3)_3]^+$, $[C_5(CH_3)_5 M'(CH_3COCH_3)_3]^+$, $[C_5(CH_3)_5M'Cl]_4$, or polymeric $[C_5(CH_3)_5M'Cl_2]_x$.

Alternatively the 6π-aromatic ring of the pincer ligand may be a cyclopentadienyl substituted in position 2,5 by Lewis base ligands indirectly attached to the cyclopentadienyl ring through a bridge. Compounds of the invention wherein the 6π-aromatic ring of the pincer ligand is cyclopentadienyl or substituted cyclopentadienyl may include binuclear species of formula (II) or trinuclear complexes of formula (III)

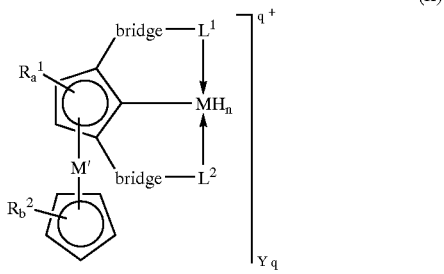

(II)

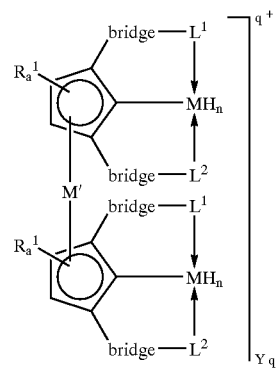

(III)

wherein:

M is Rh, Ir;

M' is Fe, Ru, Os;

$L^1$ and $L^2$ independently of one another are —PR'R", —As R'R" or —Sb R'R"; wherein R' and R" independently of one another are wherein R' and R" independently of one another are an optionally substituted alkyl, an optionally substituted cycloalkyl, and an optionally substituted aryl, or heteroaryl.

each bridge is the same or different and is a diradical;

$R^1$ and $R^2$ independently of one another are hydrogen, optionally substituted $C_1$–$C_4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where $R^1$s and $R^2$s may be the same or different and when ortho to each other can together form a saturated, unsaturated or aromatic cyclic structure which can be substituted and contain heteroatoms.

a is the number of substituents $R^1$ and is ranging from 0 to 2 inclusive;

b is the number of substituents $R^2$ and is ranging from 0 to 5 inclusive;

n is an integer equal to 2 when M is Rh and equal to 2 or 4 when M is Ir;

q is an integer ranging from 0 to 1 depending on the oxidation state of M'; and

Y is a counter anion that provides the required charge balance.

Compounds of formula (II) or (III) may be prepared by reacting a complex of transition metal M with the following metallocene intermediates of formula (V) and (VI) respectively:

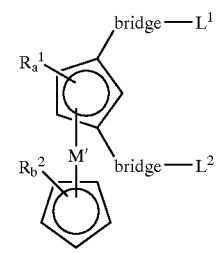

(V)

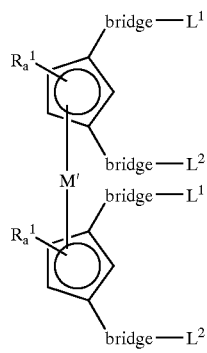

(VI)

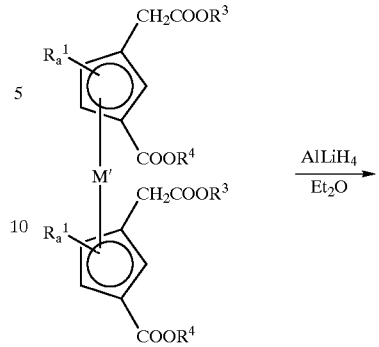

wherein M', L¹, L², R¹, R², a, b, are defined as previously. Compounds of formula (II) or (III) where M is rhodium may for example be obtained by reaction of (V) or (VI) respectively with $RhCl_3, 3H_2O$. Compounds of formula (II) or (III) where M is rhodium or iridium may for example be obtained by reaction of (V) or (VI) respectively with $[MCl(C_8H_{14})_2]_2$ followed by a hydrogenation step that substitutes the chloride ligands on M with hydride ligands. Experimental conditions to carry out the hydrogenation step may vary depending on the intermediate obtained from the reaction of (V) or (VI) with $[MCl(C_8H_{14})_2]_2$. For example the reaction of $(C_5H_5)Fe\{C_5H_4(CH_2P^iPr_2)_2\}$ with $[RhCl(C_8H_{14})2]_2$ in 2-methoxyethanol gives $(C_5H_5)Fe\{C_5H_4(CH_2P^iPr_2)_2\text{-Rh}(CO)Cl_2\}$. To obtain $C_5H_5)Fe\{C_5H_4(CH_2P^iPr_2)_2RhH_2\}$ hydrogenation may be carried out thermally or in presence of $Me_3NO$ to remove the carbonyl ligand on the rhodium centre. Alternatively, compounds (II) may be obtained by reaction of (V) with $[MCl(COE)_2(\text{solvent})_n]BF4$ (M=Rh, Ir; COE=cyclooctene; solvent=tetrahydrofuran or acetonitrile) followed by hydrogenation in presence of triethylamine.

Metallocenes of formula (V) and (VI) in which the Lewis bases are phosphino groups may be prepared according to Scheme I:

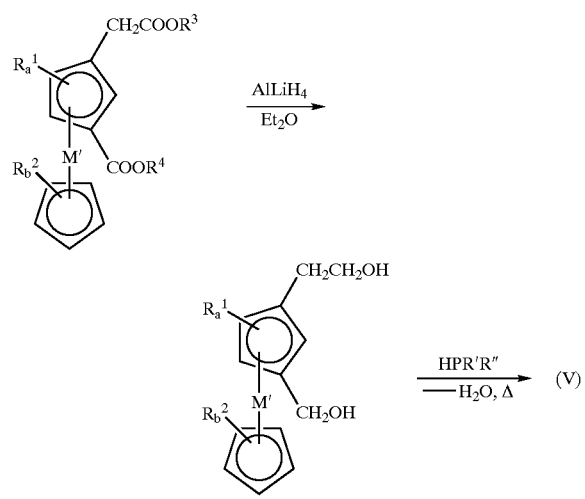

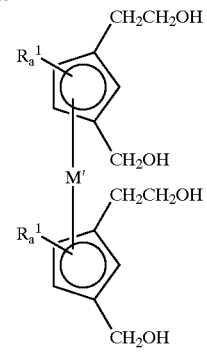

$R^3, R^4$ = Me, Et

The di- or tetra ester substituted dicyclopentadienyl metallocenes may be obtained by reacting a mixture of $C_5H_5^-$ and $[(COOR3)(COOR4)1,4-C_5H_3]^-$ with a source of transition metal M'. The novel 1,3-diestercyclopentadienyl anions may be obtained according to the following route.

$Ph_3P + BrCH_2C(Me)=CHCOOR^4 \longrightarrow$ $Br^\ominus\ Ph_3\overset{\oplus}{P}\ CH_2C(Me)=CHCOOR^4$ $\underset{OH^\ominus}{\overset{NaHCO_3}{\Big\downarrow}} ClCH_2COCH_2COOR$ The compounds of formulae (I)–(III) may be useful as catalysts for the dehydrogenation of alkanes and alkane groups. Such reactions may for example be carried out at temperature of about 60° C. to about 250° C. to produce the corresponding olefins. In alternative embodiments, the compounds of the invention may be used to catalyse the hydrogenation of unsaturated substrates. By combination of the two reactions, dehydrogenation of alkanes and alkane groups, and hydrogenation of alkenes and other unsaturated hydrocarbons, hydrogen can be cyclically stored and released for applications.

Experimental Procedures
General Comments

All reactions were carried out under an atmosphere of pure argon. Solvents were dried and distilled under nitrogen immediately before use. All $^1H$, $^{31}P$ spectra were recorded on a Bruker AM-400 spectrometer operating at 400.1 and 161.9 MHz for the respective nuclei. Infrared spectra were run on a Bruker IFS-113 spectrometer. Mass spectrometry spectra were run on Kratos MS-30 spectrometer.

Synthesis of (Cyclopentadienyl)(p-xylene)iron(II) hexafluorophosphate

A three-necked round bottomed flask, provided with a magnetic stirrer, a reflux condenser, a dropping funnel and an argon inlet, was charged with 1.86 g (10 mmol) of ferrocene, 0.27 g of aluminum powder, 2.66 g (20 mmol) of aluminum chloride, 23 ml (19.96 g, 188 mmol) of p-xylene and 0.5 ml of concentrated hydrochloric acid. The stirred reaction mixture was refluxed for 3 hours. After cooling, 50 ml of water was added, the reaction mixture was filtered, and transferred into a separating funnel. The aqueous layer after separation from the organic phase was treated with 1.63 g (10 mmol) of ammonium hexafluorophosphate. A green powder resulted which was collected on a sintered glass funnel and dried. The product was purified on a short alumina chromatography column. Elution with a 25:4 mixture of dichloro-ethane-ethanol afforded, after evaporation to dryness, 1.65 g (44.5%) of green crystals.

Synthesis of 1-Ethoxycarbonyl-3-formylferrocene

A round bottomed flask provided with a reflux condenser and an argon bubbler, was charged with a solution of 0.79 g (2.12 mmol) of (cyclopentadienyl)-(p-xylene)iron(II) hexafluorophosphate and 0.615 g (3.8 mmol) of 2-ethoxycarbonyl-6-dimethylaminopentafulvene in 40 ml of dichloromethane. The mixture was irradiated for 6 hours with an UV lamp OKH-11™ in an argon atmosphere while being stirred. The heat of the lamp caused the solvent to boil. After the mixture was cooled to room temperature, 15 ml of ethanol and 15 ml 2N NaOH were added and stirring was continued for 1.5 hours. After separation between the organic and aqueous layers, the aqueous layer was diluted to 60 ml and extracted with dichloromethane. The combined organic layers were washed twice with water, dried over $Na_2SO_4$ and concentrated. The residue was chromatographed over a short alumina column with a 1:1 mixture of ether-light petroleum eluent. The first pale red band afforded, after evaporation to dryness, 0.30 g (48%) of red crystals.

Synthesis of 1,3-bis(hydroxymethyl)ferrocene

To a stirring suspension of 60 mg (15.7 mmol) of lithium aluminum hydride in 30 ml of ether was added dropwise to a solution of 150 mg (0.56 mmol) of 1-ethoxycarbonyl-3-formylferrocene in ether (30 ml). Stirring was continued for 4.5 hours at room temperature. The mixture was then quenched with saturated aqueous solution of $NH_4Cl$, and 30 ml of ether was added to the resulting solution. After separation of the organic and aqueous layers, the latter was extracted twice with ether and the combined organic solutions were then washed with water and dried over $Na_2SO_4$. Evaporation of the solvent yielded 100 mg (77.5%) of yellow crystals. Selected NMR data $^1H$ (acetone-d6, 22° C.): δ4.11 (s, 5H,$C_5H5$), 4.13 (d, 2H, 4.5-H), 4.25 (t,1H, 2-H), 429 (s, 4H, $CH_2$)

Synthesis of 1,3-bis{(diisopropylphosphanyl)methyl}ferrocene 2.46 g (10 mmol) of 1,3-bis(hydroxymethyl)ferrocene and 4.72 g (40 mmol) of diisopropylphosphine were added to 40 ml of acetic acid. The resulting mixture was heated at 80° C. for 3.5 hours and extracted with benzene after cooling. The organic phase was then washed with water and then dried over $Na_2SO_4$. After evaporation an orange residue was chromatographed on an alumina column. Elution with an ether-light petroleum mixture yielded 3.92 g (88%) of the product. Selected NMR data (CDCl$_3$, 22° C.) $^1H$: δ0.92 (m, 24H, CH$_3$), 1.63 (m, 4H, CH(CH$_3$)$_2$), 2.49 (bs, 4H, CH$_2$P), 3.92 (s, 5H, C$_5$H$_5$), 3.95 (bs, 2H, 4.5-H), 4.06 (bs, 1H, 2-H). $^{31}$P NMR (CDCl$_3$, 22° C.): δ 10.97(s, 2P).

Synthesis of 1,3-bis(diisopropylphosphinomethane)-2-(rhodiumcarbonyldichloride)-ferrocene (C$_5$H$_5$)Fe{C$_5$H$_4$(CH$_2$P$^i$Pr$_2$)$_2$Rh(CO)Cl$_2$}

To a solution of 1,3-bis(diisopropylphosphinomethane) ferrocene (23 mg, 0.050 mmol) in 2-methoxyethanol (10 ml) was added 20 ml of 2-methoxyethanol solution of [Rh (C$_8$H$_{14}$)$_2$Cl]$_2$ (18 mg, 0.025 mmol). The mixture refluxed for 1 hour. The solvent was evaporated under vacuum and the resulting yellow residue was extracted with toluene. The toluene extract was passed through a small alumina column and the yellow residue eluted with hexane. A yellow band was collected from which 12 mg of 1,3-bis(diisopropylphosphinomethane)-2-(rhodiumcarbonyldichloride)ferrocene, was recovered as yellow crystals. Spectroscopic data for (C$_5$H$_5$)Fe{C$_5$H$_4$(CH$_2$P$^i$Pr$_2$)$_2$Rh(CO)Cl$_2$}: $^1$H NMR (CDCl$_3$, 22° C.): δ 4.15 (s, 2H, CH FePCP), 4.01 (s, 5H, FeC$_5$H$_5$), 3.30 (m, 2H, CH $^i$Pr), 2.99 (dt, $^2$J$_{HH}$=16.4 Hz, $^3$j$_{HP}$=3.5 Hz, 2H, CHHP), 2.82 (dt, $^2$J$_{HH}$=16.4 Hz, $^3$J=4.6 Hz, 2H CHHP), 2.77 (m, 2H, CH $^i$Pr), 1.74 (dd, $^3$J$_{HH}$=7.6 Hz, $^3$J$_{HH}$=15.7 Hz, 6H, CH$_3$ $^i$Pr), 1.62 (m, 12H, CH$_3$ $^i$Pr), 1.37 (dd, $^3$J$_{HH}$=7.2 Hz, $^3$J$_{HH}$=14.2 Hz, 6H, CH$_3$ $^i$Pr). $^{31}$P NMR (CDCl$_3$, 22° C.): δ 62.61 (d, J$_{PRh}$=82.8 Hz). IR (CH$_2$Cl$_2$) ν$_{CO}$ 2055 cm$^{-1}$(s). MS (M$^+$—CO) 618.

Synthesis of [{1-Methoxycarbonyl-2-methyl-4-ethoxymethylcarbonyl}cyclo-pentadienyl] (pentamethylcyclopentadienyl)ruthenium A solution of 1-methoxycarbonyl-2-methyl-4-ethoxymethylcarbonylcyclopentadienyl sodium was generated from stirring 3 g (13.38 mmol) of ethyl 4-methoxycarbonyl-3-methylcyclopenta-1,3-dienylacetate (prepared according to the procedure reported in *J. Chem. Soc., Perkin Trans-I*, 1993, 2269) and 0.64 g (16.1 mmol) of NaH (60% in mineral oil) in THF (150 ml) in argon atmosphere at −78° C. After 0.5 hours 1.03 g (3.34 mmol) of complex [Ru(C$_5$Me$_5$)Cl$_2$]$_n$ was added to the solution which was then allowed to warm-up to room temperature. After stirring for 4 hours the solution was evaporated and the resulting residue was chromatographed over an alumina column with light petroleum as the eluent. A broad pale yellow band afforded, after evaporation to dryness and crystallization from a 4:1 n-hexane-dichloromethane mixture, 1.1 g (71%) of pale yellow crystals. Spectroscopic data for [{1-Methoxycarbonyl-2-methyl-4-ethoxymethylcarbonyl}cyclo-pentadienyl](pentamethylcyclopentadienyl)ruthenium: $^1$H NMR (CDCl$_3$): δ 1.22 (t, J=7.1, 3H, CH$_2$,CH$_3$), 1.72 (s, 15H, CH$_3$), 1.97 (s, 3H, CH$_3$), 2.98 (d, J=15.8, 1H, CH$^A$CH$^B$COOEt), 3.01, (d, J=15.8, 1H, CH$^A$CH$^B$COOEt), 3.70 (s, 3H, OCH$_3$), 4.09 (q, J=7.1, 2H, CH$_2$CH$_3$), 4.27 (d, J=1, 1H, 3-H), 4.66 (d, J=1.5, 1H, 5-H).

Synthesis of {1-Hydroxymethyl-2-methyl-4-(2'-hydroxyethyl)cyclopentadienyl}-(pentamethylcyclopentadienyl) ruthenium To stirring suspension of 67 g (1.78 mmol) of LiAlH$_4$ in 15 ml of ether was added dropwise to a solution of 510 mg (1.12 mmol) of [{1-methoxycarbonyl-2-methyl-4-ethoxymethylcarbonyl}cyclopentadienyl] (pentamethylcyclopentadienyl)ruthenium in 15 ml of ether. After stirring for 2.5 hours at room temperature the mixture was quenched with saturated aqueous NH$_4$Cl. After separation, the aqueous layer was extracted twice with ether and the combined etheral solutions were then washed with water and dried over Na$_2$SO$_4$. Evaporation of ether yielded 340 mg (87.3%) of white crystals. Spectroscopic data for {1-Hydroxymethyl-2-methyl-4-(2'-hydroxy-ethyl)cyclopentadienyl}(pentamethylcyclopentadienyl)ruthenium: $^1$H NMR (CDCl$_3$): δ 1.74 (s, 3H, CH$_3$), 1.88 (s, 15H, CH$_3$), 2.21 (t, J=6.4, C$\underline{H}_2$CH$_2$OH), 3.65 (m, CH$_2$C$\underline{H}_2$OH) 3.93 (bd, J=11.3, 1H, C$\underline{H}^A$(H$^B$)OH), 3.99 (bs, 1H, 3(5)-H), 4.03 (dd, j=11.3, 4.4, 1H, CH$^A$($\underline{H}^B$)OH), 4.13 (bs, 1H, 5(3)-H).

Synthesis of [{1-(diisopropylphosphanyl)methyl}(2-methyl){4-(2'-diisopropyl-phosphanyl)ethyl}cyclopentadienyl](pentamethylcyclopentadienyl)ruthenium 1.37 g (3.54 mmol) of {1-hydroxymethyl-2-methyl-4-(2'-hydroxyethyl)cyclopenta-dienyl}(pentamethylcyclopentadienyl)ruthenium and 0.84 g (7.08 mmol) of diisopropylphosphine were added to 20 ml of glacial acetic acid. The mixture was heated for 1 hour at 80° C. then cooled and extracted with toluene. The dried (Na$_2$SO$_4$) extracts were evaporated, and the resulting residue was chromatographed on an alumina column with a 5:1 n-hexane-ether mixture. The formed {1-(diisopropylphosphanyl)methyl}(2-methyl)-4-(2'-hydroxyethyl)(pentamethylcyclo-pentadienyl)ruthenium (identified by $^1$H and $^{31}$p NMR) was dissolved in 30 ml of THF and cooled to −78° C. A solution of n-butyllithium in hexane (2.42 ml of a 1.65M solution, 4 mmol) was slowly added to the cold stirred solution. A solution of 0.76 g (4 mmol) of p-toluenesulphonylchloride in 20 ml of THF was then added. After 1.5 hours of stirring the solution was evaporated. The resulting residue was dissolved in 30 ml of acetone, and 0.84 g (7.08 mmol) of diisopropylphosphine and 0.60 g (4.0 mmol) of sodium iodide was added to this solution. The mixture was refluxed for 4 hours and the precipitated phosphonium salt and sodium salt of para-toluenesulphonic acid were filtered off. The solid was dissolved in degassed water and treated with a solution of sodium acetate in water. After extraction with ether the product was isolated as a white solid (1.38 g, 60%).

I claim:

1. A polynuclear organometallic compound comprising a tripodal pincer ligand comprising at least one aromatic ring and two neutral Lewis bases, said Lewis bases being indirectly linked to said aromatic ring through a bridge, said pincer ligand coordinating to a first transition metal through each of the Lewis bases and having one atom σ-bonded to said first transition metal, the aromatic ring of said pincer ligand having all ring atoms π-bonded to a second transition metal.

2. A polynuclear organometallic compound comprising:
    (a) a first transition metal selected from the group consisting of Rh, Ir, said first transition metal being bonded to n hydrogen atoms, n being an integer selected such that first transition metal has an electron count of 16 or 18 electrons;
    (b) a second transition metal selected from the group consisting of Fe, Ru, Rh, Os, and Ir, said second transition metal being π-bonded to an η$^5$-aromatic ligand;
    (c) a pincer ligand comprising a 6π-electron aromatic ring having at least 2 ring atoms in an 1,3 relationship bonded each to a neutral Lewis base through a bridge, L$^1$ and L$^2$ independently of one another are —PR'R", As R'R" or —Sb R'R"; wherein R' and R" independently of one another are wherein R' and R" independently of one another are an optionally substituted alkyl, an optionally substituted cycloalkyl, and an optionally substituted aryl, or heteroaryl;
    each bridge is the same or different and is a diradical;

R$^1$ and R$^2$ independently of one another are hydrogen, optionally substituted C$_1$–C$_4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where R$^1$s and R$^2$s may be the same or different and when ortho to each other can together form a saturated, unsaturated or aromatic cyclic structure which can be substituted and contain heteroatoms;

a is the number of substituents R$^1$ and is ranging from 0 to 2 inclusive;

b is the number of substituents R$^2$ and is ranging from 0 to 5 inclusive;

n is an integer equal to 2 when M is Rh and equal to 2 or 4 when M is Ir;

q is an integer ranging from 0 to 1 depending on the oxidation state of M'; and said bridge being a diradical, and said pincer ligand binding the first transition metal through each of the Lewis base and through the ring atom adjacent to both lewis bases and having all aromatic ring atoms π-coordinated to the second transition metal through all of the aromatic ring atoms.

3. The polynuclear organometallic compound of claim 2 wherein the η$^5$-aromatic is selected from the group of cyclopentadienyl and substituted cyclopentadienyl, wherein the substituents are selected from the group consisting of optionally substituted C1–C4 alkyl, optionally substituted arylalkyl or heteroarylalkyl in which the alkyl chain contains 1 to 4 carbons, optionally substituted aryl or heteroaryl or when two substitutents are ortho to each other they can together form a saturated, unsaturated or aromatic cyclic structure which can be substituted and contain heteroatoms.

4. The polynuclear organometallic compound of claim 2 wherein the 6π-electron aromatic ring is selected from the group consisting of phenyl, substituted phenyl, cyclopentadienyl and substituted cyclopentadienyl, wherein the substituents are selected from the group consisting of optionally substituted C1–C4 alkyl, alkylsilyl in which the alkyl chains contain 1 or 2 carbons; optionally substituted arylalkyl or heteroarylalkyl in which the alkyl chain contains 1 to 4 carbons, optionally substituted aryl or heteroaryl and where the substitutents may be the same or different and when two substitutents are ortho to each other they can together form a saturated, unsaturated or aromatic cyclic structure which can be substituted and contain heteroatoms.

5. A binuclear organometallic compound of formula (I):

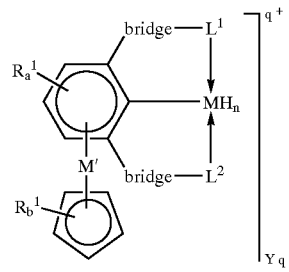

wherein:

M is Rh, Ir;

M' is Fe, Ru, Rh, Os, or Ir;

L$^1$ and L$^2$ independently of one another are —PR'R"AsR'R" or —Sb R'R"; wherein R' and R" independently of one another are wherein R' and R" independently of one another are an optionally substituted alkyl, an optionally substituted cycloalkyl, and an optionally substituted aryl, or heteroaryl;

each bridge is the same or different and is a diradical;

$R^1$ and $R^2$ independently of one another are hydrogen, optionally substituted $C_1$–$C_4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where $R^1$s and $R^2$s may be the same or different and when ortho to each other can together form a saturated, unsaturated or aromatic cyclic structure which can be substituted and contain heteroatoms;

a is the number of substituents $R^1$ and is ranging from 0 to 3 inclusive;

b is the number of substituents $R^2$ and is ranging from 0 to 5 inclusive;

n is an integer equal to 2 when M is Rh and equal to 2 or 4 when M is Ir;

q is an integer equal to 1 when M is Fe, Ru or Os and equal to 2 when M' is Rh or Ir; and Y is a counter anion that provides the required charge balance.

6. A binuclear organometallic compound of formula (II):

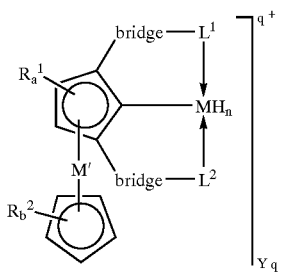

wherein:

M is Rh, Ir;

M' is Fe, Ru, Os;

Y is a counter anion that provides the required charge balance.

7. A trinuclear organometallic compound of formula III:

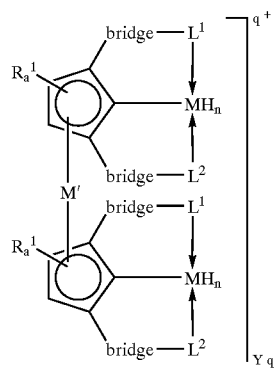

wherein:

M is Rh, Ir;

M' is Fe, Ru, Os;

$L^1$ and $L^2$ independently of one another are —PR'R", AsR'R" or —SbR'R"; wherein R' and R" independently of one another are wherein R' and R" independently of one another are an optionally substituted alkyl, an optionally substituted cycloalkyl, and an optionally substituted aryl, or heteroaryl;

each bridge is the same or different and is a diradical;

$R^1$ is hydrogen, optionally substituted $C_1$–$C_4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where $R^1$s and $R^2$s may be the same or different and when ortho to each other can together form a saturated, unsaturated or aromatic cyclic structure which can be substituted and contain heteroatoms;

a is the number of substituents $R^1$ and is ranging from 0 to 2 inclusive;

n is an integer equal to 2 when M is Rh and equal to 2 or 4 when M is Ir;

q is an integer ranging from 0 to 1 depending on the oxidation state of M'; and

Y is a counter anion that provides the required charge balance.

8. A mononuclear complex of formula V:

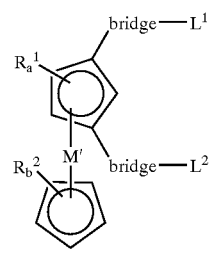

wherein:

M' is Fe, Ru, Os;

$L^1$ and $L^2$ independently of one another are —PR'R", AsR'R" or —SbR'R"; wherein R' and R" independently of one another are optionally substituted alkyl, an optionally substituted cycloalkyl, and an optionally substituted aryl, or heteroaryl;

each bridge is the same or different and is a diradical;

$R^1$ and $R^2$ independently of one another are hydrogen, optionally substituted $C_1$–$C_4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where $R^1$s and $R^2$s may be the same or different and when ortho to each other can together form a saturated, unsaturated or aromatic cyclic structure which can be substituted and contain heteroatoms;

a is the number of substituents $R^1$ and is ranging from 0 to 2 inclusive;

b is the number of substituents $R^2$ and is ranging from 0 to 5 inclusive.

9. A mononuclear complex of formula VI:

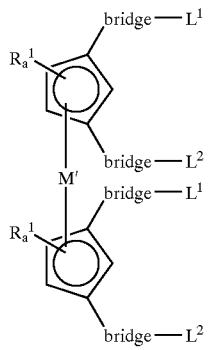

wherein:
M' is Fe, Ru, Os;
L¹ and L² independently of one another are —PR'R", AsR'R" or —SbR'R"; wherein R' and R" independently of one another are wherein R' and R" independently of one another are an optionally substituted alkyl, an optionally substituted cycloalkyl, and an optionally substituted aryl, or heteroaryl;
each bridge is the same or different and is a diradical;
$R^1$ is hydrogen, optionally substituted $C_1$–$C_4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where $R^1$s and $R^2$s may be the same or different and when ortho to each other can together form a saturated, unsaturated or aromatic cyclic structure which can be substituted and contain heteroatoms.

10. A process of converting an alkane or an alkyl-containing compound into a corresponding olefinic compound comprising contacting the alkane or alkyl-containing compound at conditions conducive to dehydrogenation with a composition comprising a polynuclear organometallic compound according to claim 1.

11. A process of converting an alkane or an alkyl-containing compound into a corresponding olefinic compound comprising contacting the alkane or alkyl-containing compound at conditions conducive to dehydrogenation with a composition comprising a binuclear organometallic compound according to claim 5.

12. A process of converting an alkane or an alkyl-containing compound into a corresponding olefinic compound comprising contacting the alkane or alkyl-containing compound at conditions conducive to dehydrogenation with a composition comprising a trinuclear organometallic compound according to claim 7.

13. A process of converting an alkane or an alkyl-containing compound into a corresponding olefinic compound comprising contacting the alkane or alkyl-containing compound at conditions conducive to dehydrogenation with a composition comprising a mononuclear organometallic compound according to claim 8.

14. A process of converting an alkane or an alkyl-containing compound into a corresponding olefinic compound comprising contacting the alkane or alkyl-containing compound at conditions conducive to dehydrogenation with a composition comprising a mononuclear organometallic compound according to claim 9.

15. The process of claim 10 comprising contacting the alkane or alkyl-containing compound with a composition comprising the binuclear organometallic compound of formula (II):

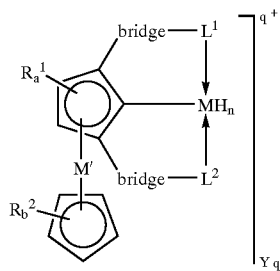

wherein:
M is Rh, Ir;
M' is Fe, Ru, Os;
L¹ and L² independently of one another are —PR'R", As R'R" or —Sb R'R"; wherein R' and R" independently of one another are wherein R'and R" independently of one another are an optionally substituted alkyl, an optionally substituted cycloalkyl, and an optionally substituted aryl, or heteroaryl;
each bridge is the same or different and is a diradical;
$R^1$ and $R^2$ independently of one another are hydrogen, optionally substituted $C_1$–$C^4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where $R^1$s and $R^2$s may be the same or different and when ortho to each other can together form a saturated, unsaturated or aromatic cyclic structure which can be substituted and contain heteroatoms;
a is the number of substituents $R^1$ and is ranging from 0 to 2 inclusive;
b is the number of substituents $R^2$ and is ranging from 0 to 5 inclusive;
n is an integer equal to 2 when M is Rh and equal to 2 or 4 when M is Ir;
q is an integer ranging from 0 to 1 depending on the oxidation state of M'; and
Y is a counter anion that provides the required charge balance.

16. The process of claim 11 comprising contacting the alkane or alkyl-containing compound with a composition comprising the binuclear organometallic compound of formula (II):

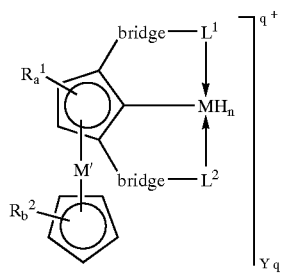

wherein:
M is Rh, Ir;
M' is Fe, Ru, Os;
L¹ and L² independently of one another are —PR'R", As R'R" or —Sb R'R"; wherein R' and R" independently of one another are wherein R' and R" independently of one another are an optionally substituted alkyl, an optionally substituted cycloalkyl, and an optionally substituted aryl, or heteroaryl;

each bridge is the same or different and is a diradical;

$R^1$ and $R^2$ independently of one another are hydrogen, optionally substituted $C_1$–$C_4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where $R^1$s and $R^2$s may be the same or different and when ortho to each other can together form a saturated, unsaturated or aromatic cyclic structure which can be substituted and contain heteroatoms;

a is the number of substituents $R^1$ and is ranging from 0 to 2 inclusive;

b is the number of substituents $R^2$ and is ranging from 0 to 5 inclusive;

n is an integer equal to 2 when M is Rh and equal to 2 or 4 when M is Ir;

q is an integer ranging from 0 to 1 depending on the oxidation state of M'; and

Y is a counter anion that provides the required charge balance.

17. The process of claim 12 comprising contacting the alkane or alkyl-containing compound with a composition comprising the binuclear organometallic compound of formula (II):

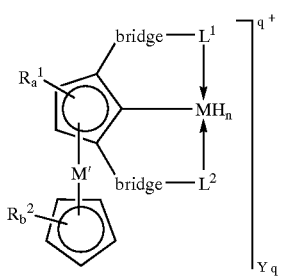

wherein:

M is Rh, Ir;

M' is Fe, Ru, Os;

$L^1$ and $R^2$ independently of one another are —PR'R", As R'R" or —Sb R'R"; wherein R' and R" independently of one another are wherein R' and R" independently of one another are an optionally substituted alkyl, an optionally substituted cycloalkyl, and an optionally substituted aryl, or heteroaryl;

each bridge is the same or different and is a diradical;

$R^1$ and $R^2$ independently of one another are hydrogen, optionally substituted $C_1$–$C_4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where $R^1$s and $R^2$s may be the same or different and when ortho to each other can together form a saturated, unsaturated or aromatic cyclic structure which can be substituted and contain heteroatoms;

a is the number of substituents $R^1$ and is ranging from 0 to 2 inclusive;

b is the number of substituents $R^2$ and is ranging from 0 to 5 inclusive;

n is an integer equal to 2 when M is Rh and equal to 2 or 4 when M is Ir;

q is an integer ranging from 0 to 1 depending on the oxidation state of M'; and

Y is a counter anion that provides the required charge balance.

18. The process of claim 13 comprising contacting the alkane or alkyl-containing compound with a composition comprising the binuclear organometallic compound of formula (II):

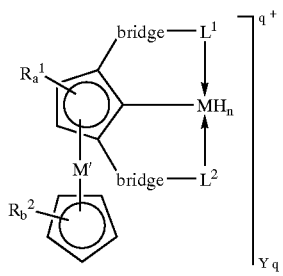

wherein:

M is Rh, Ir;

M' is Fe, Ru, Os;

$L^1$ and $L^2$ independently of one another are —PR'R", As R'R" or —Sb R'R"; wherein R' and R" independently of one another are wherein R' and R" independently of one another are an optionally substituted alkyl, an optionally substituted cycloalkyl, and an optionally substituted aryl, or heteroaryl;

each bridge is the same or different and is a diradical;

$R^1$ and $R^2$ independently of one another are hydrogen, optionally substituted $C_1$–$C_4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where $R^1$s and $R^2$s may be the same or different and when ortho to each other can together form a saturated, unsaturated or aromatic cyclic structure which can be substituted and contain heteroatoms;

a is the number of substituents $R^1$ and is ranging from 0 to 2 inclusive;

b is the number of substituents $R^2$ and is ranging from 0 to 5 inclusive;

n is an integer equal to 2 when M is Rh and equal to 2 or 4 when M is Ir;

q is an integer ranging from 0 to 1 depending on the oxidation state of M'; and

Y is a counter anion that provides the required charge balance.

19. The process of claim 14 comprising contacting the alkane or alkyl-containing compound with a composition comprising the binuclear organometallic compound of formula (II):

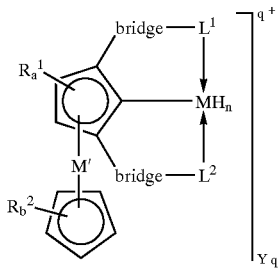

wherein:

M is Rh, Ir;

M' is Fe. Ru, Os;

L¹ and L² independently of one another are —PR'R", As R'R" or —Sb R'R"; wherein R' and R" independently of one another are wherein R' and R" independently of one another are an optionally substituted alkyl, an optionally substituted cycloalkyl, and an optionally substituted aryl, or heteroaryl;

each bridge is the same or different and is a diradical;

R¹ and R² independently of one another are hydrogen, optionally substituted $C_1$–$C_4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where R¹s and R²s may be the same or different and when ortho to each other can together form a saturated, unsaturated or aromatic cyclic structure which can be substituted and contain heteroatoms;

a is the number of substituents R¹ and is ranging from 0 to 2 inclusive;

b is the number of substituents R² and is ranging from 0 to 5 inclusive;

n is an integer equal to 2 when M is Rh and equal to 2 or 4 when M is Ir;

q is an integer ranging from 0 to 1 depending on the oxidation state of M'; and

Y is a counter anion that provides the required charge balance.

20. A method of using a polynuclear organometallic compound comprising the steps of (a) providing a polynuclear organometallic compound comprising a tripodal pincer ligand comprising at lest one aromatic ring and two neutral Lewis bases, said Lewis bases being indirectly linked to said aromatic ring through a bridge, said pincer ligand coordinating to a first transition metal through each of the Lewis bases and having one atom σ-band to said first transition metal, the aromatic ring of said pincer ligand having all ring atoms π-bonded to a second transition metal; and (b) using the compound of step (a) to cyclically store and release hydrogen.

21. A process for the preparation of a binuclear organometallic compound of formula (I):

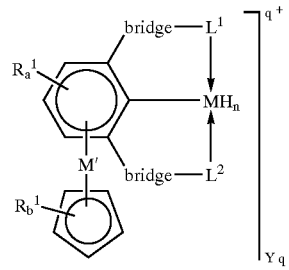

wherein:

M is Rh, 1r

M' is Fe, Ru, Rh, Os, or Ir;

L¹ and L² independently of one another are —PR'R", AsR'R" or —Sb R'R"; wherein R' and R" independently of one another are wherein R' and R" independently of one another are an optionally substituted alkyl, an optionally substituted cycloalkyl, and an optionally substituted aryl, or heteroaryl;

each bridge is the same or different and is a diradical;

R¹ and R² independently of one another are hydrogen, optionally substituted $C_1$–$C_4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where R¹s and R²s may be the same or different and when ortho to each other can together form a saturated, unsaturated or aromatic cyclic structure which can be substituted and contain heteroatoms;

a is the number of substituents R¹ and is ranging from 0 to 3 inclusive;

b is the number of substituents R² and is ranging from 0 to 5 inclusive;

n is an integer equal to 2 when M is Rh and equal to 2 or 4 when M is Ir;

q is an integer equal to 1 when M is Fe, Ru or Os and equal to 2 when M' is Rh or lr and Y is a counter anion that provides the required charge balance Said process comprising reacting in a solvent a mononuclear complex of formula (IV):

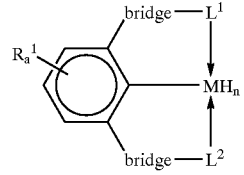

wherein:

M is Rh, or Ir;

L¹ and L² independently of one another are —PR'R", AsR'R" or —SbR'R"; wherein R' and R" independently of one another are wherein R' and R" independently of one another are an optionally substituted alkyl, an optionally substituted cycloalkyl, and an optionally substituted aryl, or heteroaryl;

each bridge is the same or different and is a diradical;

$R^1$ and $R^2$ independently of one another are hydrogen, optionally substituted $C_1$–$C_4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where $R^1$s and $R^2$s may be the same or different and when ortho to each other can together form a saturated, unsaturated or aromatic cyclic structure which can be substituted and contain heteroatoms;

a is the number of substituents $R^1$ and is ranging from 0 to 3 inclusive n is an integer equal to 2 when M is Rh and equal to 2 or 4 when M is Ir;

with a source of (Ar)M' wherein M' is defined as previously and Ar is a $R^2_b$ substituted $\eta^5$-cyclopentadienyl ligand π-bonded to M' where $R^2$ and b are defined as previously.

22. A process for the preparation of a binuclear organometallic compound of formula (I):

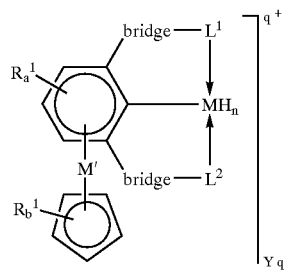

wherein:

M is Rh, Ir;

M' is Fe, Ru, Rh, Os, or Ir;

$L^1$ and $L^2$ independently of one another are —PR'R", AsR'R" or —Sb R'R"; wherein R' and R" independently of one another are wherein R' and R" independently of one another are an optionally substituted alkyl, an optionally substituted cycloalkyl, and an optionally substituted aryl, or heteroaryl;

each bridge is the same or different and is a diradical;

$R^1$ and $R^2$ independently of one another are hydrogen, optionally substituted $C_1$–$C_4$ alkyl, alkylsilyl in which the alkyl chains contain 1 or 2 carbons, optionally substituted arylalkyl or heteroarylalkyl in which the alkyl chain contains 1 to 4 carbons, optionally substituted aryl or heteroaryl and where $R^1$s and $R^2$s may be the same or different and when ortho to each other can together form a saturated, unsaturated or aromatic cyclic structure which can be substituted and contain heteroatoms;

a is the number of substituents $R^1$ and is ranging from 0 to 3 inclusive;

b is the number of substituents $R^2$ and is ranging from 0 to 5 inclusive;

n is an integer equal to 2 when M is Rh and equal to 2 or 4 when M is Ir;

q is an integer equal to 1 when M is Fe, Ru or Os and equal to 2 when M' is Rh or Ir; and Y is a counter anion that provides the required charge balance said process comprising reacting In a solvent under inert atmosphere a mononuclear complex of the formula $H_nM\{C_6R^1_3\text{-}2,6(CH_2PR_2)_2\}$, wherein M is Ir or Rh; $R^1$ is H or $CH_3$; n is 2 when M is Rh and 2 or 4 when M is Ir, and R is tert-butyl, isopropyl, or cyclohexyl with a source of $M'\{\eta^5\text{-}C_5(CH_3)_5\}$.

* * * * *